United States Patent [19]

Westphal et al.

[11] Patent Number: 4,694,978
[45] Date of Patent: Sep. 22, 1987

[54] APPARATUS AND METHOD FOR SIMULTANEOUSLY INVERTING, FOLDING AND PLEATING

[75] Inventors: Dean W. Westphal; David T. Strohbeen, both of Appleton, Wis.

[73] Assignee: Kimberly-Clark Corporation, Neenah, Wis.

[21] Appl. No.: 916,256

[22] Filed: Oct. 7, 1986

[51] Int. Cl.$^4$ .......................... A41C 5/00; D06C 15/00
[52] U.S. Cl. ........................................ 223/28; 223/37; 223/40; 493/313
[58] Field of Search ....................... 223/28, 37, 38, 39, 223/40, 43; 493/313

[56] References Cited

U.S. PATENT DOCUMENTS

| | | | |
|---|---|---|---|
| 1,331,546 | 2/1920 | Wagner | 223/40 |
| 1,378,646 | 5/1921 | Baum | 223/40 |
| 3,310,207 | 3/1967 | Gore | 223/39 |
| 3,446,121 | 5/1969 | Achelpohl | 493/313 |
| 3,965,647 | 6/1976 | Sjoman | 223/37 X |
| 3,977,580 | 8/1976 | Vecchia | 223/43 |
| 4,180,190 | 12/1979 | Flaum et al. | 223/43 |
| 4,223,816 | 9/1980 | Glover | 223/37 |
| 4,249,972 | 2/1981 | Barth | 223/39 X |
| 4,401,244 | 8/1983 | Selvi et al. | 223/37 |
| 4,460,111 | 7/1984 | Nakahira | 223/43 |
| 4,596,544 | 6/1986 | Hull | 493/313 |

Primary Examiner—Louis K. Rimrodt
Attorney, Agent, or Firm—Douglas L. Miller; Donald L. Traut; Jeremiah J. Duggan

[57] ABSTRACT

Apparatus and method are provided for simultaneously folding and pleating a child's training pant or the like. The apparatus generally includes a plunger that is reciprocative through a tube member. The tube member has an interior surface defining an interior space and a pleating surface disposed on the interior surface. Upon the plunger member forcibly urging the training pant through the interior space, it is simultaneously folded by the interior surface and pleated by the pleating surfaces.

15 Claims, 12 Drawing Figures

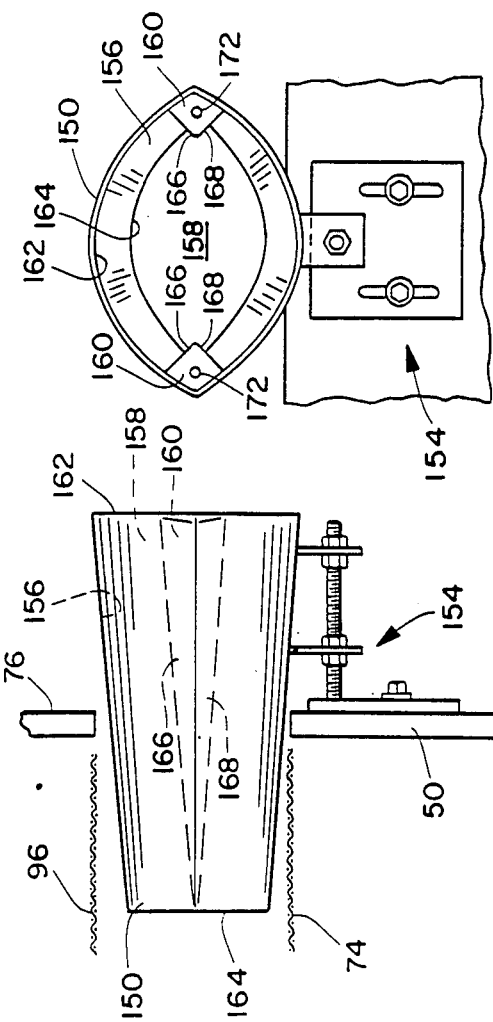
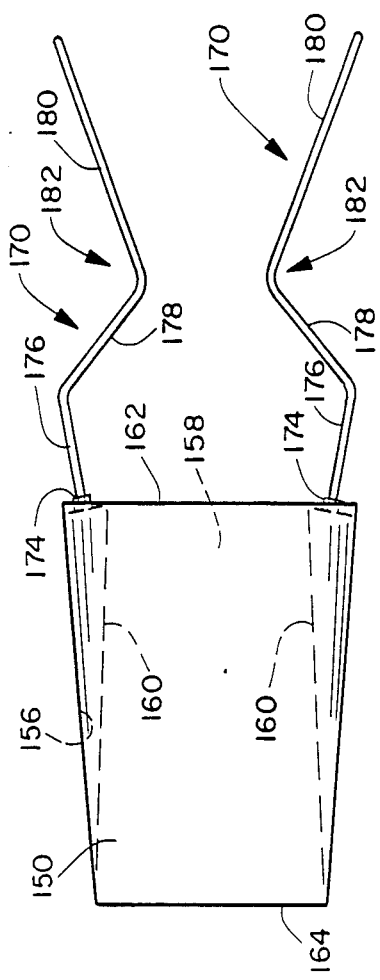
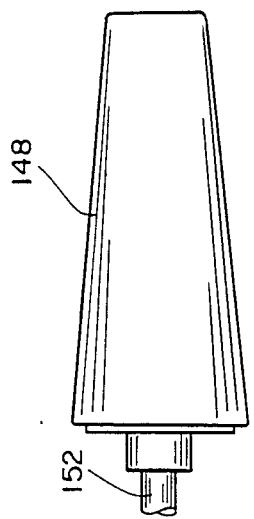
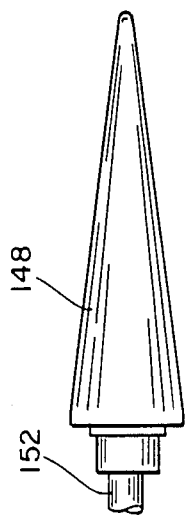

APPARATUS AND METHOD FOR SIMULTANEOUSLY INVERTING, FOLDING AND PLEATING

BACKGROUND OF THE INVENTION

This invention pertains to an apparatus and method for handling a child's training pant or the like, and more particularly to an apparatus and method for inverting and simultaneously folding and pleating a child's training pant or the like.

A child's training pant generally comprises a crotch area that joins a front panel and back panel that have their side edges joined together to form a pair of generally oppositely disposed seams. Generally it is desired for the training pant to be turned or inverted so that the seams are inwardly disposed of the pant body, thereby presenting a pant having a pleasing look, among other things.

After the training pant has been inverted, or in those cases where inverting the pant is unnecessary and the seams can remain on the outside thereof, it is generally desired to fold and pleat the pant into a compact form for subsequent handling and packaging. One manner of inverting or folding and pleating a child's training pant is to peform it manually. This process is naturally time-consuming and costly in terms of expended manhours and downtime of machinery used to subsequently handle or package the training pant.

Some apparatus and methods exist for inverting different types of garments, such as hose, or other objects such as bags. In one such type of apparatus and method, the hose or bag is manually placed over a hollow tube and a plunger is then passed through the tube to invert the hose or bag. Thereafter, the hose or bag is manually removed.

In another type of apparatus and method, a hose or bag is manually placed over a tube or the upstanding collar of an opening, and a vacuum or sucking action is used to draw the hose or bag through the tube or opening, thereby inverting it.

In another type of apparatus and method, gripping members or tongs are used to grip the side edges of the opening of an object to hold it open, and a plunger device is moved against the opposite closed end to pass it between the gripping members or tongs, thereby inverting the object.

In the above-described apparatus and methods, the inverting procedure is time-consuming where manual operations must be performed, and thus costly due to excess manhours and machinery downtime. Furthermore, there is no provision for simultaneously folding and pleating the hose or bag or other object, whether it has been inverted previously or not.

Thus, the need exists for an apparatus and method that inverts a child's training pant or the like, and simultaneously folds and pleats the training pant, in an efficient and less-costly manner.

SUMMARY OF THE INVENTION

The present invention provides, in one form thereof, an apparatus and method for simultaneously folding and pleating a child's training pant or the like, which may or may not have been previously inverted.

In one form of the present invention, there is provided an apparatus for simultaneously folding and pleating a child's training pant or the like comprising a handling station adapted for selectively positioning a pant thereat, a plunger member at the handling station and being selectively reciprocative thereacross, and a folding mechanism having an interior surface defining an interior space for receiving therein the plunger member upon reciprocation thereof and a pleating device disposed on the interior surface adapted for pleating a pant passed thereover.

In another form of the present invention, there is provided a method for simultaneously folding and pleating a child's training pant or the like comprising the steps of providing a handling station, providing a plunger member that is selectively reciprocative cross the handling station, and providing a folding device at the handling station, the folding device including an interior surface defining an interior space for receiving the reciprocating plunger member and a pleating surface disposed on the interior surface thereof. The method further includes positioning a pant at the handling station, reciprocating the plunger member against the pant, and simultaneously folding and pleating the pant as it is urged into and through the interior space and over the pleating surface of the folding device.

It is an object of the present invention to provide an apparatus that simultaneously folds and pleats a child's training pant or the like.

Another object of the present invention is to provide a method that simultaneously folds and pleats a child's training pant or the like.

Yet another object of the present invention is to provide an apparatus and method for simultaneously folding and pleating a child's training pant or the like in a more efficient and less-costly manner.

BRIEF DESCRIPTION OF THE DRAWINGS

The above-mentioned and the other features and objects of this invention, and the manner of attaining them, will become more apparent and the invention itself will be better understood by reference to the following description of an embodiment of the invention taken in conjunction with the accompanying drawings, wherein:

FIG. 3 is a side elevational view of a portion of the folding and pleating assembly in FIG. 1;

FIG. 4 is an end elevational view of the portion in FIG. 3;

FIG. 5 is a top plan view of the folding and pleating cone with pleating rods attached;

FIG. 6 is a top plan view of the plunger head in FIG. 1;

FIG. 7 is a side elevational view of the plunger head in FIG. 6;

DESCRIPTION OF A PREFERRED EMBODIMENT

Figure 1:
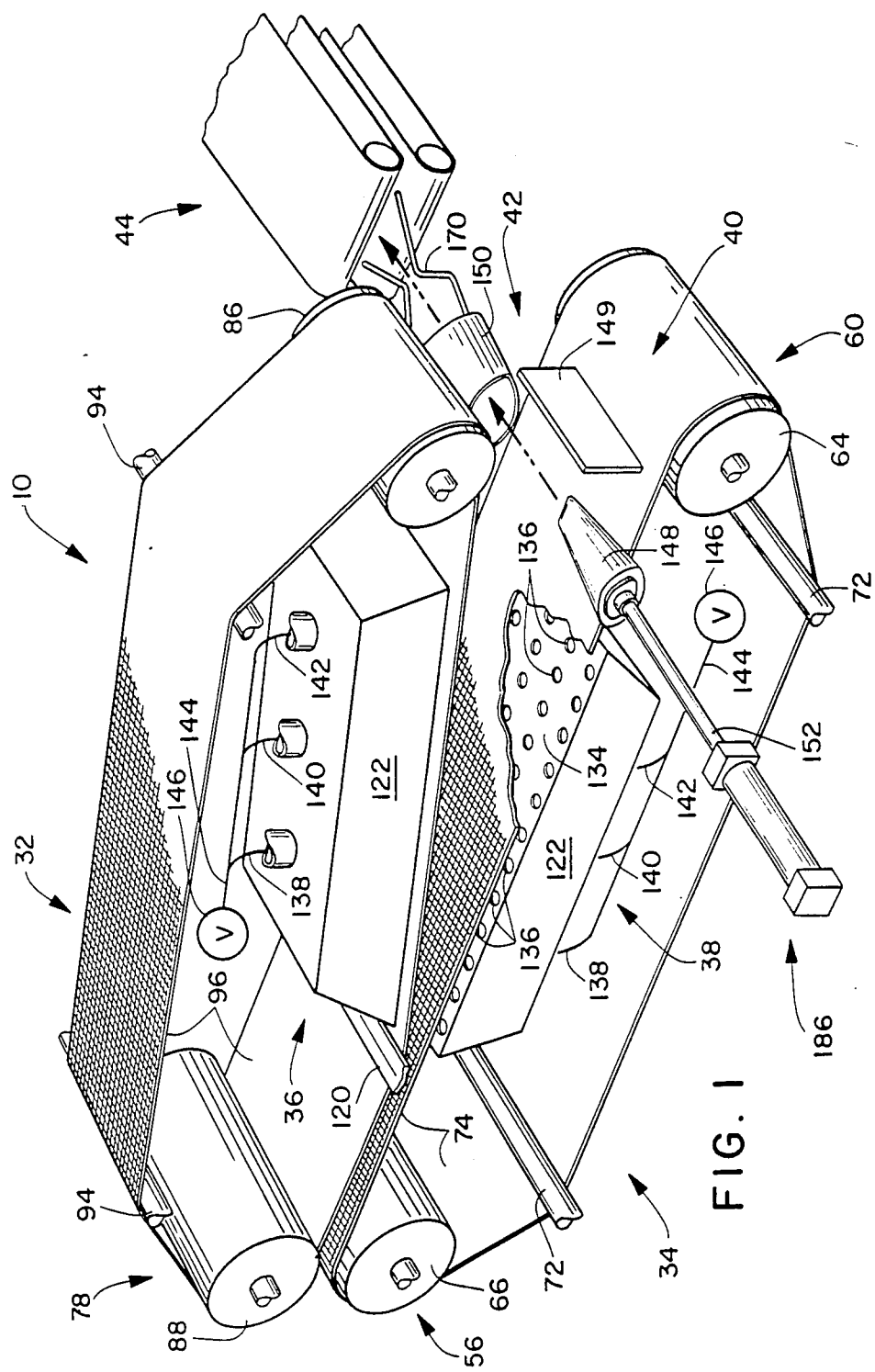
FIG. 1 is a perspective view of an apparatus which may be operated according to the principles of the present invention.
Figure 2:
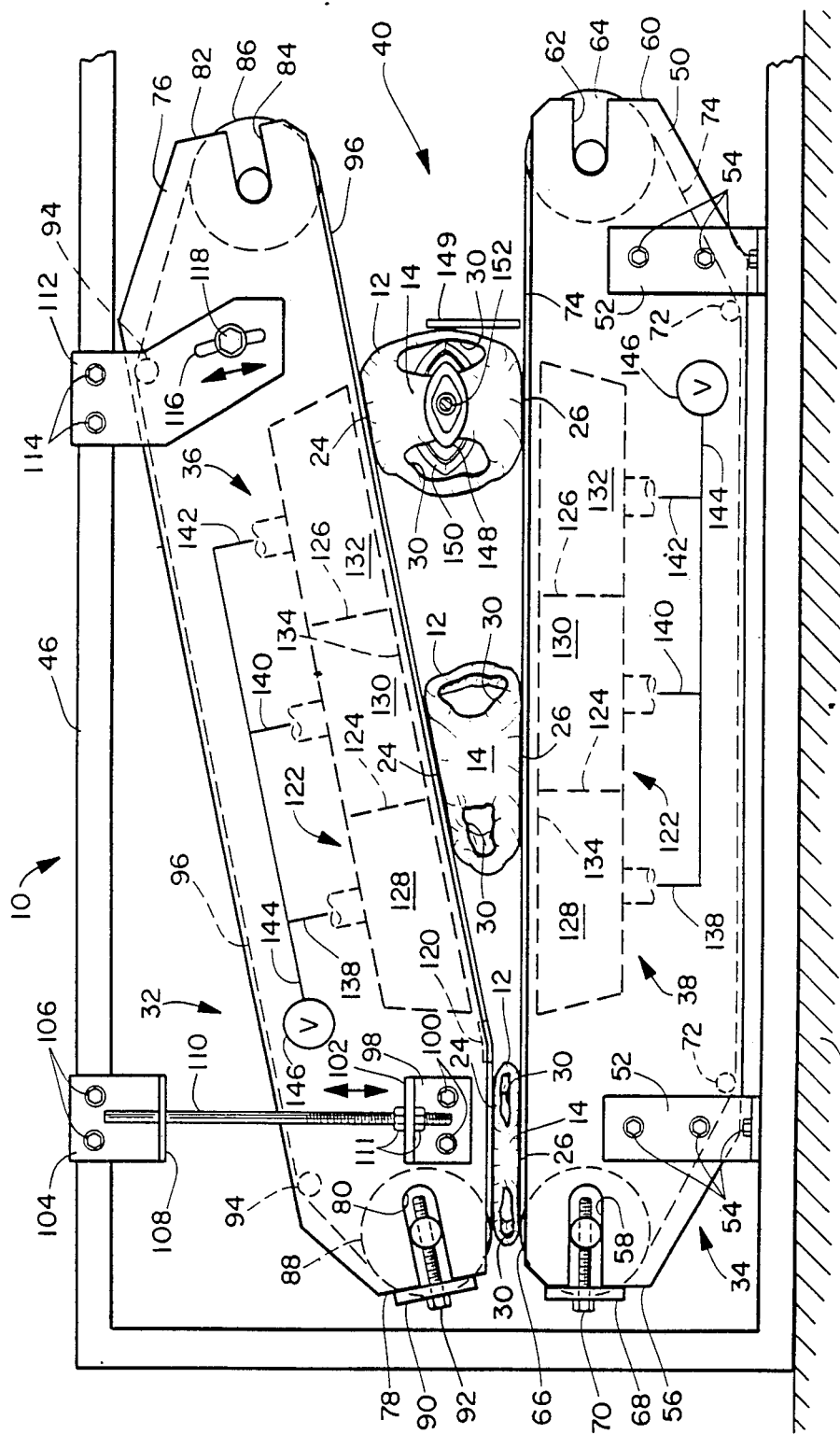
FIG. 2 is an elevational view of the apparatus of FIG. 1 mounted for operation.
Figure 8:
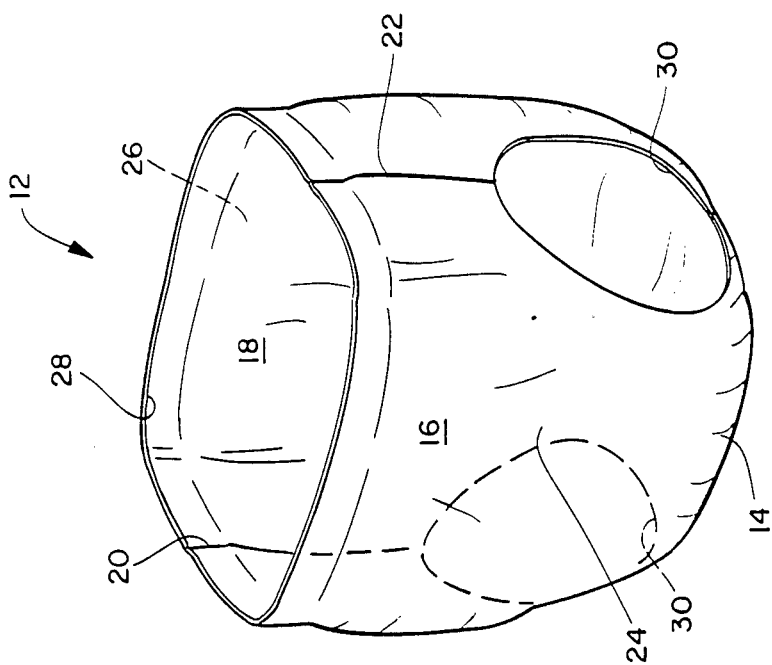
FIG. 8 is a perspective view of a child's training pant.

Referring to FIGS. 1 and 2, there is illustrated an apparatus 10 which may be operated according to the principles of the present invention. FIG. 8 illustrates training pant 12 which can be inverted and then simultaneously folded and pleated by the present invention. Training pant 12 generally comprises crotch portion 14 joining front panel 16 and back panel 18, which are joined together at side seams 20, 22. Front panel 16 includes exterior surface portion 24 and back panel 18 includes exterior surface portion 26. Training pant 12 further comprises waist opening 28 and a pair of leg openings 30.

Apparatus 10 comprises in major part a pair of mutually facing conveyor assemblies 32, 34, a pair of suction systems 36, 38 associated with a respective conveyor assembly 32, 34, handling station 40, folding and pleating assembly 42, and transfer conveyor assembly 44.

Referring primarily to FIG. 2, conveyor assemblies 32, 34 are mounted within support frame 46, which is suitably secured to foundation 48. Conveyor assembly 34 includes a pair of side mounting plates 50, only one of which is illustrated, which are spaced-apart and generally parallel to each other. Each side mounting plate 50 is secured to support frame 46 by a pair of mounting brackets 52 and associated bolts 54. Since both side mounting plates 50 are identical, a description of only one side mounting plate 50 will be made. Each side mounting plate 50 includes a starting end portion 56 having a slot 58 and a finishing end portion 60 having a slot 62. Slots 62 slidably and rotatably receive drive roll 64 therein, and slots 58 slidably and rotatably receive adjustable take-up roll 66 therein. Drive roll 64 can be driven by any suitable and conventional means, and take-up roll 66 can be horizontally adjusted, as viewed in FIG. 2, by means of take-up bracket 68 and bolt 70. Take-up roll 66 is connected to take-up bracket 68, and by loosening bolt 70, take-up roll 66 can be selectively adjusted in slot 58. Thereafter, bolt 70 can be tightened against take-up bracket 68 to secure take-up roll 66 in slot 58. A pair of idler rolls 72 extend between and are rotatably connected to side mounting plates 50.

Bottom conveyor belt 74 is tightly disposed against drive roll 64, take-up roll 66, and idler rolls 72. Bottom conveyor belt 74 is continuously run in a clock-wise rotation, as viewed in FIG. 2, by drive roll 64. Although the term "belt" is used in describing bottom conveyor belt 74, it is to be understood that bottom conveyor belt 74 can be a solid material or a porous material, and in the preferred embodiment is a screen mesh (FIG. 1). Conveyor assembly 32 is generally similar to conveyor assembly 34, and includes a pair of oppositely disposed and generally parallel side mounting plates 76, only one of which is illustrated, and each has a starting end portion 78 having a slot 80 and a finishing end portion 82 having a slot 84. Drive roll 86 is slidably and rotatably received in slot 84, and take-up roll 88 is slidably and rotatably received in slot 80 and is adjustable therein by means of take-up bracket 90 and bolt 92 in a manner similar to take-up roll 66. A pair of idler rolls 94 extends between and are rotatably connected to side mounting plates 76. Top conveyor belt 96 is tightly disposed against drive roll 86, take-up roll 88, and idler rolls 94, and is driven in a counter-clockwise direction by drive roll 86. Similar to bottom conveyor belt 74, top conveyor belt 96 is preferably made of a screen mesh.

Although conveyor assemblies 32, 34 are illustrated in FIGS. 1 and 2 as being mounted vertically relative to each other, the present invention contemplates other spatial orientations, such as assemblies 32, 34 being disposed on their sides such that conveyor belts 74, 96 are generally perpendicular to foundation 48. In the preferred embodiment, conveyor assembly 32 is mounted above conveyor assembly 34 within support frame 46. Since side mounting plates 76 are identically mounted within frame 46, a description of the adjustable mounting of only one side mounting plate 76 will be made. Support bracket 98 is secured to side mounting plate 76, such as by bolts 100, and has an outwardly extending flange 102 with a hole (not shown) disposed therein. Hanger bracket 104 is secured to support frame 46, such as by bolts 106, and has an outwardly extending flange 108 with an opening (not shown) disposed therein. Flanges 102, 108 are substantially parallel and have their respective holes (not shown) concentrically aligned. Threaded rod 110 is received through the opening in flange 108 and secured therein, such as by welding or brazing or the like, and its opposite threaded end is slidably received in the opening of flange 102. A pair of nuts 111 are threadedly received on threaded rod 110 such that the top nut 111 is above flange 102 and the bottom nut 111 is below flange 102.

Although not illustrated, a similar hanger bracket 104, support bracket 98 and threaded rod 110 may also be provided at the finishing end portion 82 of side mounting plates 76. This permits conveyor assembly 32 to be vertically adjusted relative to conveyor assembly 34 by loosening nuts 111 and sliding conveyor assembly 32 upwardly or downwardly along threaded rod 110. Once the desired distance between conveyor assemblies 32, 34 is attained, nuts 111 can be tightly threaded against flanges 102, thereby securing conveyor assembly 32.

Illustrated in FIG. 2 at finishing end portion 82 is support plate 112 secured to support frame 46, such as by bolts 114. The bottom portion of support plate 112, which is adjacent a respective side mounting plate 76, has an arcuate slot 116 in alignment with an opening (not shown) in side mounting plate 76. Support bolt 118 is received through the opening (not shown) in side mounting plate 76 and through arcuate slot 116, and has a nut (not shown) threadedly engaged on its remote end. Although not illustrated, a similar support plate 112 and support bolt 118 can be provided at the starting end portion 78. By loosening one or both of the support bolts 118, conveyor assembly 32 can be pivotally adjusted relative to conveyor assembly 34. For example, should it be desired to elevate finishing end portion 82 upwardly relative to conveyor assembly 34, all of the support bolts 118 may be loosened, thereby allowing finishing end portion 82 to be pivoted upwardly while maintaining starting end portion 78 at its original position. Thereafter, support bolts 118 may be tightened to secure conveyor assembly 32.

The present invention also contemplates securing conveyor assembly 32 with a combination of the above-described mounting methods so that conveyor assembly 32 can be both vertically and pivotally adjusted relative to conveyor assembly 34. Various types of adjustments can be necessary to accommodate different size or types of training pants.

As presently illustrated in FIGS. 1 and 2, an idler bar 120 extends between side mounting plates 76 and against top conveyor belt 96 to cause top conveyor belt 96 to substantially parallel bottom conveyor belt 74 along the distance between take-up roll 88 and idler bar 120. Finishing end portion 82 of conveyor assembly 32 has been pivoted upwardly so that conveyor belts 74, 96 diverge in a direction from idler bar 120 to respective finishing end portions 60, 82.

Suction systems 36, 38 are respectively associated with conveyor assemblies 32, 34 and since they are virtually identical, both will carry the same reference numerals and a description of only one suction system will be made. Further, if conveyor assembly 32 is adjusted vertically or pivotally, suction system 36 is designed to move therewith.

Continuing to refer primarily to FIGS. 1 and 2, suction system 36 comprises a suction chamber 122 being divided by partitions 124, 126 into three suction compartments 128, 130, 132. Wall 134 (FIG. 1) of suction system 36, which is identical to wall 134 of suction system 38, has a plurality of openings 136 therein for allowing fluid communication between suction chamber 122 and the outside atmosphere. The present invention also contemplates wall 134 being made of a screen mesh identical or similar to the screen mesh of which conveyor belts 74, 96 are made. Each suction compartment 128, 130, 132 is respectively connected by vacuum lines 138, 140, 142 to master vacuum line 144, which is connected to vacuum source 146. Throughout the specification, the term "vacuum" is meant to be the same as "suction" or "drawing". Thus, it is to be understood that the two suction chambers 122 do not create a vacuum between conveyor assemblies 32, 34, but create a suction or drawing force toward their respective conveyor belts 74, 96.

The suction or drawing force of each vacuum source 146 can be provided in any suitable manner, such as by fans or pumps of different types. Furthermore, a plurality of vacuum sources 146 can be provided such that each individual vacuum line 138, 140, 142 has its own individually controlled vacuum source. Whether a single or plurality of vacuum sources 146 are utilized, the suction force provided by a vacuum source 146 is variable in strength by, for example, varying the fan or pump speed. This allows a selective variation of the suction force in a generally perpendicular direction relative to a respective conveyor belt 74, 96.

The suction force provided by suction system 36 can also vary linearly, i.e., in the direction of movement of a respective conveyor belt 74, 96, which is generally a direction from starting end portion 78 to finishing end portion 82. This can be accomplished by varying the number and/or size of openings 136 in suction compartments 128, 130, 132. Also, the suction force may be varied linearly in this direction by providing each vacuum line 138, 140, 142 with its own vacuum source 146, and then selectively controlling the suction forces of vacuum sources 146 to vary the suction force in the direction of movement of belts 74, 96. Thus, by selectively controlling a single or plurality of vacuum sources 146, the suction force provided by a respective suction system 36, 38 can be simultaneously varied in a direction generally perpendicular to its respective conveyor belt 74, 96 and in the direction of movement of belts 74, 96.

Referring now primarily to FIGS. 1, 3–6, folding and pleating assembly 42 is located at handling station 40 and generally comprises plunger head 148 reciprocatively operated by pneumatic assembly 186, and folding and pleating cone 150 disposed on the opposite side of conveyor assemblies 32, 34 and in axial alignment with plunger head 148. Both plunger head 148 and cone 150 are laterally and vertically adjustable relative to the space between conveyor assemblies 32, 34 so as to be adaptable to different sizes or types of training pants. Stop plate 149 is selectively positionable along belt 74 to accommodate different sizes or types of training pants 12.

Plunger head 148 is connected by shaft 152 to pneumatic assembly 186, which selectively reciprocates plunger head 148 in a sequential fashion. Referring to FIGS. 6 and 7, plunger head 148 is generally wedge-shaped (FIG. 7) and tapers from its proximate end to its distal end at an angle between 10°–20°, and optimally 15°.

Referring now to FIGS. 3–5, folding and pleating cone 150 has a general shape of a truncated cone of oval cross-section. The angle of cone 150 with respect to its central longitudinal axis is between about 3°–10°, and optimally 5°. Although cone 150 is shaped as a truncated cone, it can also have other types of shapes, such as a generally cylindrical shape, and have different cross-sections, such as various polygonal cross-sections. Cone 150 is supported on side mounting plate 50 (FIG. 3) by adjustable support bracket assembly 154, which permits cone 150 to be adjusted laterally and vertically.

Folding and pleating cone 150 has interior surface 156 defining interior space 158 therein. Mounted on the oblong ends of interior surface 156 are a pair of pleating surfaces 160 which taper from end opening 162 toward start opening 164 of cone 150. As viewed in FIG. 5, each pleating surface 160 tapers from a position wherein it extends inwardly of interior space 158 at end opening 162 to a position near start opening 164 wherein it coincides or is flush with interior surface 156. Each pleating surface 160 comprises a top surface 166 and a bottom surface 168, which are angularly joined and are adapted contact and impinge against opposite side portions of a training pant being urged through start opening 164 by plunger head 148. Start opening 164 has a frontal area less than the area of training pant 12 taken in a plane in an intermediate portion thereof, such as a plane including the side seams 20, 22 of an expanded training pant 12 or including waist opening 28 of an expanded training pant 12, as viewed in FIG. 8.

A pair of pleating rods 170 are secured to respective pleating surfaces 160 and extend outwadly from end opening 162 of cone 150. Pleating rods 170 are identical, and only a description of one will be made. A pleating rod 170 is threadedly received in a threaded opening 172 in the end of pleating surface 160 and secured therein by a nut 174. Each pleating rod 170 is formed such that it has a first segment 176 which is angled outwardly of cone 150, a second segment 178 which is angled inwardly of cone 150, and a third segment 180 which is angled outwardly, thereby forming a curved portion 182. Matching curved portions 182 are adapted to received the pleated fold of a folded and pleated training pant 12 after it has exited end opening 162 and prepares it for removal by transfer conveyor assembly 44.

The various angular relationships given or illustrated can be varied as desired for a particular size or type of training pant. For example, pleating surfaces 160 can taper at varying angles toward interior surface 165; top and bottom surfaces 166, 168 can be angularly joined at different angles; and segments 176, 178, 180 of a pleating rod 170 can be varied as necessary to maintain and fold a training pant. Similarly, the linear dimensions of plunger head 148, cone 150, pleating surfaces 160, and pleating rods 170 can be varied as a function of the type and size of training pant 12. Training pant sizes vary to accommodate different age and size children.

Referring now primarily to FIGS. 1, 2, and 10–12, the operation of apparatus 10 will be described. In FIG. 2, a training pant 12 has been transferred to starting end portions 56, 78 in a compressed, but unfolded and unpleated, condition. As training pant 12 is moved by conveyor belts 74, 96, the suction force created by top and bottom suction compartments 128 begins to separate pant exterior surface portions 24, 26 and to draw them against the diverging portions of belts 74, 96. As pant 12 continues its movement, the suction forces provided by top and bottom suction compartments 130 also begin to act on exterior surface portions 24, 26 to expand pant 12 further open. This continues until training pant 12 is completely opened under the suction force of top and bottom suction compartments 132. Once pant 12 is fully opened, its movement is hindered by stop plate 149.

Before proceeding further, it should be pointed out that the versatility of apparatus 10 allows it to operate on various types and sizes of training pants 12. For example, if a larger training pant 12 is to be handled, then conveyor assembly 32 can be adjusted upwardly and, if necessary, pivotally relative to conveyor assembly 34. Since a larger training pant 12 will have a larger expanded configuration, conveyor assembly 32 will require this adjustment. Furthermore, the suction forces provided by suction systems 36, 38 can be varied in a direction generally normal to a respective conveyor belt 74, 96 and/or in a direction of movement of training pant 12. Generally, a larger training pant will require greater suction forces in order to expand the greater mass of the larger pant.

Once training pant 12 is at handling station 40, pneumatic assembly 186 is sequentially operated to move plunger head 148 against training pant 12. Continued operation on training pant 12 can occur in two different fashions, depending upon whether pant 12 needs to be inverted or not. If side seams 20, 22 are on the outside of pant 12 and it is desired to invert pant 12 so that side seams 20, 22 are inwardly disposed of pant 12, then plunger head 148 will first contact crotch portion 14 (FIG. 2) and begin to urge it through start opening 164 (FIG. 3) of cone 150. Further movement of plunger head 148 will then cause training pant 12 to be fully inverted as it passes through cone 150.

If it is not desired to invert training pant 12, or it is preferred to leave side seams 20, 22 extending outwardly from training pant 12, then pant 12 can be introduced to apparatus 10 such that waist opening 28 faces plunger head 148. Movement of plunger head 148 will then be initially through waist opening 28 (FIG. 10) and contact the interior portion of crotch portion 14, thereby progressively urging training pant 12 through folding and pleating cone 150. It should be pointed out at this point that the suction forces provided by suction systems 36, 38 need to be strong enough to hold a training pant 12 to be inverted while plunger head 148 contacts the exterior surface of crotch portion 14 and begins to move pant 12.

Figure 10:
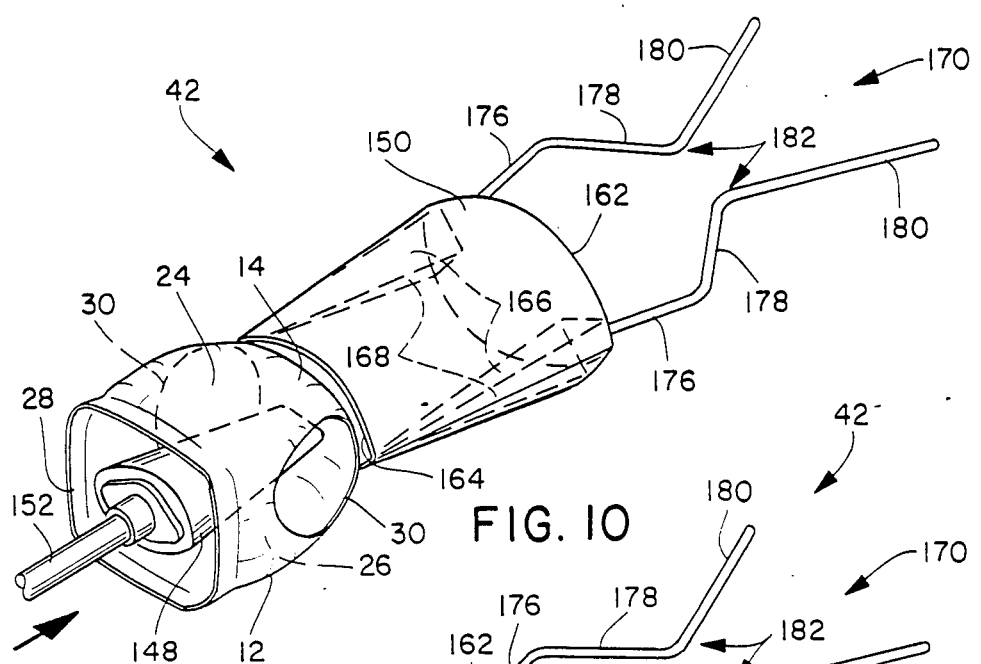
FIG. 10 is a perspective view illustrating the plunger head inside the training pant prior to its entry into the folding and pleating cone.
Figure 11:
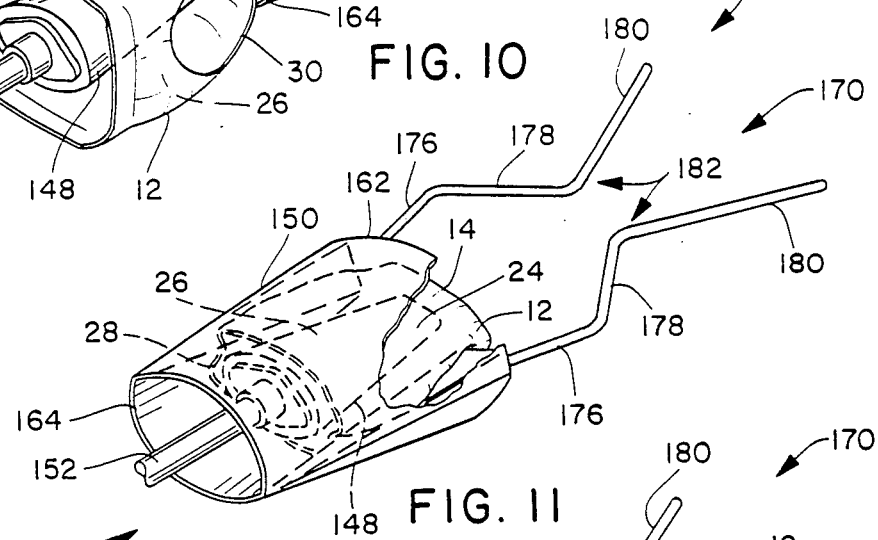
FIG. 11 is a perspective view similar to FIG. 10 with the training pant inside the folding and pleating cone.
Figure 12:
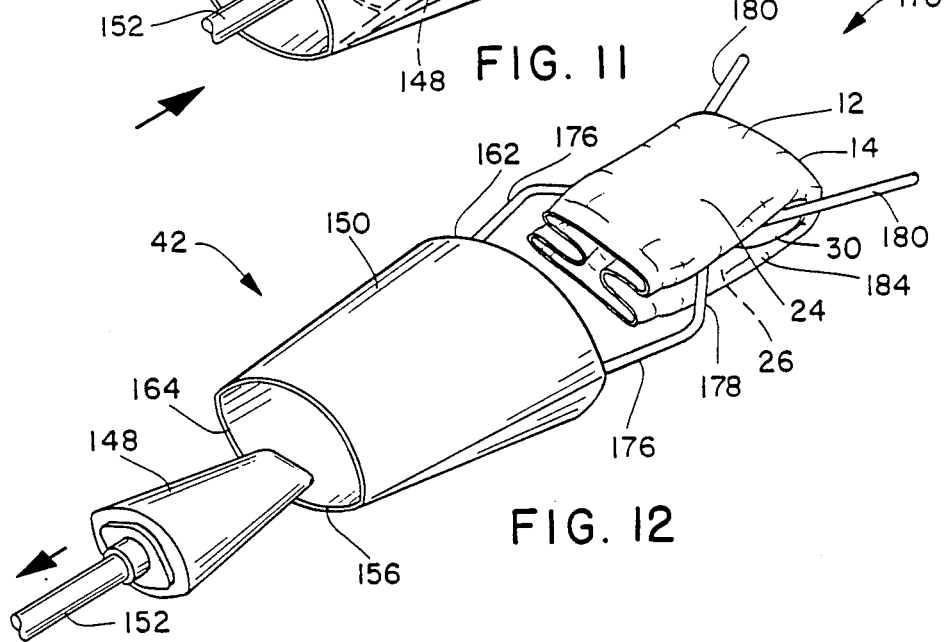
FIG. 12 is a perspective view similar to FIG. 10 with the folded and pleated training pant disposed on the pleating rods.

Regardless of the orientation of training pant 12, once plunger head 148 continues to urge pant 12 through cone 150, pant 12 is progressively and simultaneously folded by interior surface 156 and pleated along side seams 20, 22 by pleating surfaces 160. FIG. 11 illustrates training pant 12 just beginning to exit end opening 162 in a folded and pleated configuration. (FIGS. 10–12 illustrate a pant 12 not needing to be inverted.)

After plunger head 148 has moved training pant 12 through end opening 162, pleating rods 170 hold and maintain training pant 12 in its folded and pleated condition. This is accomplished by curved portions 182 nesting in respective pleated folds 184. Thereafter, transfer conveyor assembly 44 removes the folded and pleated training pant 12.

Figure 9:
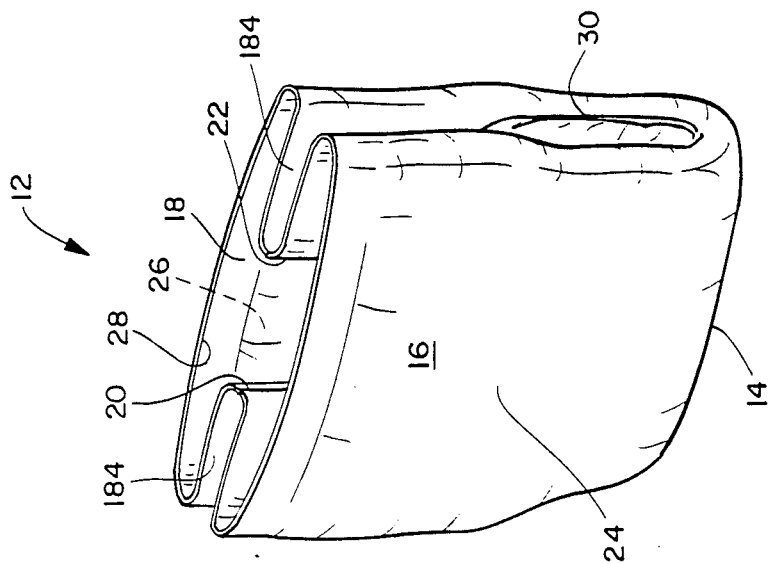
FIG. 9 is a perspective view of the training pant in FIG. 8 after it has been folded and pleated.

As described, it can now be appreciated that apparatus 10, operated in accordance with the principles of the present invention, efficiently opens a training pant 12 by means of suction systems 36, 38 and then moves the pant by means of conveyor belts 74, 96 to handling station 40. Folding and pleating assembly 42 then inverts, if necessary, the opened training pant 12 and then simultaneously folds and pleats training pant 12, as illustrated in FIG. 9 for subsequent handling and packaging.

While this invention has been described as having a preferred embodiment, it will be understood that it is capable of further modifications. This application is therefore intended to cover any variations, uses, or adaptations of the invention following the general principles thereof, and including such departures from the present disclosure as come within known or customary practice in the art to which this invention pertains and fall within the limits of the appended claims.

What is claimed is:

1. Apparatus for simultaneously folding and pleating a child's training pant or the like, comprising:
   a handling station adapted for selectively positioning a pant thereat,
   a plunger member at said handling station and being selectively reciprocative thereacross, and
   a folding means at said handling station and having an interior surface defining an interior space for receiving therein said plunger member upon reciprocation thereof, and a pleating means disposed on said interior surface adapted for pleating a pant passed thereover, whereby said plunger member can be reciprocated against the pant to move the pant into said interior space to be simultaneously folded by said folding means and pleated by said pleating means.

2. The apparatus of claim 1 wherein said pleating means is a pair of generally elongate pleating surfaces being disposed on generally opposite portions of said interior surface and extending inwardly of said interior space, whereby said pleating surfaces pleat portions of the pant passed thereover.

3. The apparatus of claim 1 wherein said folding means is a generally elongate tube member having oppositely disposed open ends, said plunger member being reciprocative through said open ends, one of said open ends having an area less than an area of the pant taken on a plane passing through an intermediate portion of the pant, whereby the pant is folded upon being forcibly urged through said one open end by said plunger member.

4. The apparatus of claim 3 wherein said interior surface of said tube member diverges from said one open end to the other of said open ends.

5. The apparatus of claim 4 wherein said pleating means includes a pair of generally elongate pleating surfaces being disposed on generally opposite portions of said interior surface and extending inwardly of said interior space, said pleating surfaces tapering from said other open end to said one open end of said tube member, whereby said pleating surfaces pleat portions of the pant passed thereover.

6. The apparatus of claim 5 wherein said pleating means further includes a holding means at said other open end of said tube member and adapted for holding and maintaining the pant in its folded and pleated configuration after passing through said other open end.

7. The apparauts of claim 6 wherein said holding means includes a pair of rod members extending longitudinally outwardly from said tube member, said rod members having curved portions thereof adapted to be positioned in the pleated portions of the pant.

8. The apparatus of claim 7 further comprising a conveyor means adjacent said rod members and being adapted for conveying the folded and pleated pant from said rod members.

9. The apparatus of claim 8 wherein said tube member is oval shaped in cross section.

10. The apparatus of claim 1 wherein said plunger member is generally wedge-shaped.

11. A method for simultaneously folding and pleating a child's training pant or the like, comprising the steps of:
   providing a handling station for a pant,
   providing a plunger member that is selectively reciprocative across the handling station,
   providing a folding device at the handling station, the folding device including an interior surface defining an interior space for receiving the reciprocative plunger member and a pleating surface disposed on the interior surface,
   positioning a pant at the handling station,
   reciprocating the plunger member against the pant, and
   simultaneously folding and pleating the pant as it is urged into and through the interior space and over the pleating surface of the folding device.

12. The method of claim 11 wherein the step of providing the folding device includes the step of diverging the interior surface in the direction of reciprocation of the plunger member against the pant.

13. The method of claim 12 wherein the step of providing the folding device includes the step of tapering the pleating surface in a direction generally opposite to the direction of reciprocation of the plunger member against the pant.

14. The method of claim 11 further comprising the step of maintaining the pant in its folded and pleated condition after passing through the folding device.

15. The method of claim 14 further comprising the step of conveying the maintained folded and pleated pant from the handling station.

* * * * *